United States Patent
Martinez et al.

(10) Patent No.: US 7,295,940 B2
(45) Date of Patent: *Nov. 13, 2007

(54) PROCESS CONTROL SYSTEM TO MANAGE MATERIALS USED IN CONSTRUCTION

(75) Inventors: David Frederick Martinez, Cypress, TX (US); Elias George ElDahdah, Houston, TX (US)

(73) Assignee: Atser, Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 11/120,672

(22) Filed: May 2, 2005

(65) Prior Publication Data
US 2005/0192692 A1    Sep. 1, 2005

Related U.S. Application Data

(63) Continuation of application No. 10/349,433, filed on Jan. 21, 2003, now Pat. No. 6,889,148.

(51) Int. Cl.
*G01N 37/00* (2006.01)

(52) U.S. Cl. .................................................. 702/83
(58) Field of Classification Search ................ 702/83, 702/84; 700/97, 106; 73/78; 701/29
See application file for complete search history.

(56) References Cited

U.S. PATENT DOCUMENTS

| | | | |
|---|---|---|---|
| 5,943,234 A * | 8/1999 | Martinez et al. ............... 700/97 |
| 5,952,561 A * | 9/1999 | Jaselskis et al. ................ 73/78 |
| 6,484,079 B2 * | 11/2002 | Buckelew et al. ............. 701/29 |
| 6,687,559 B2 * | 2/2004 | Radjy et al. ................. 700/106 |
| 2002/0138220 A1 * | 9/2002 | Birkner et al. ................ 702/84 |

* cited by examiner

*Primary Examiner*—Bryan Bui
*Assistant Examiner*—Xiuqin Sun
(74) *Attorney, Agent, or Firm*—Tran & Associates

(57) ABSTRACT

Systems and methods are disclosed for designing and tracking construction material usage by estimating volumetric properties for one or more mix designs; determining an optimum mix based on laboratory data; and field testing a sample of the optimum mix; and tracking and managing construction material usage based on the optimum mix.

20 Claims, 3 Drawing Sheets

Process for Designing and Tracking Construction Material

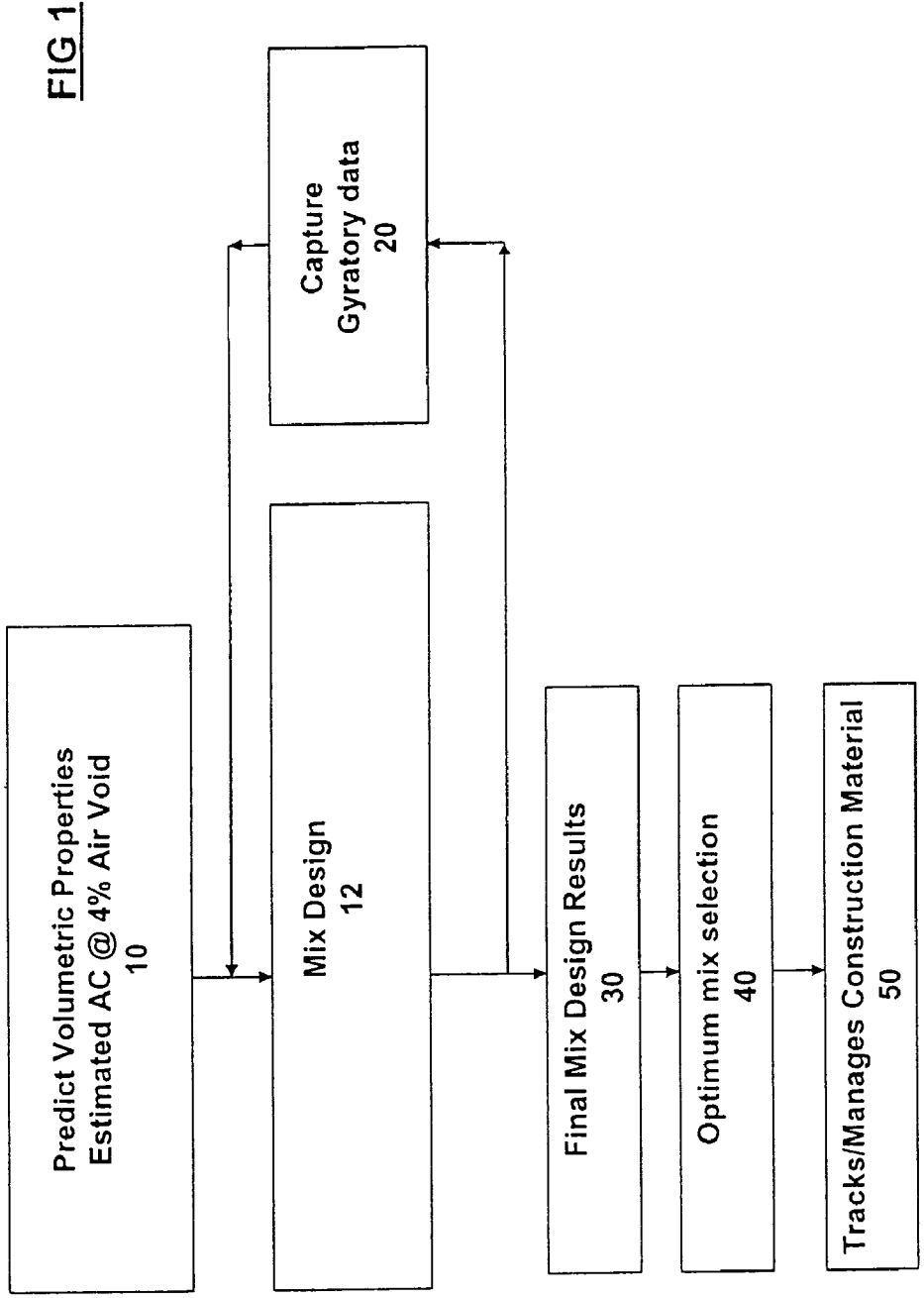

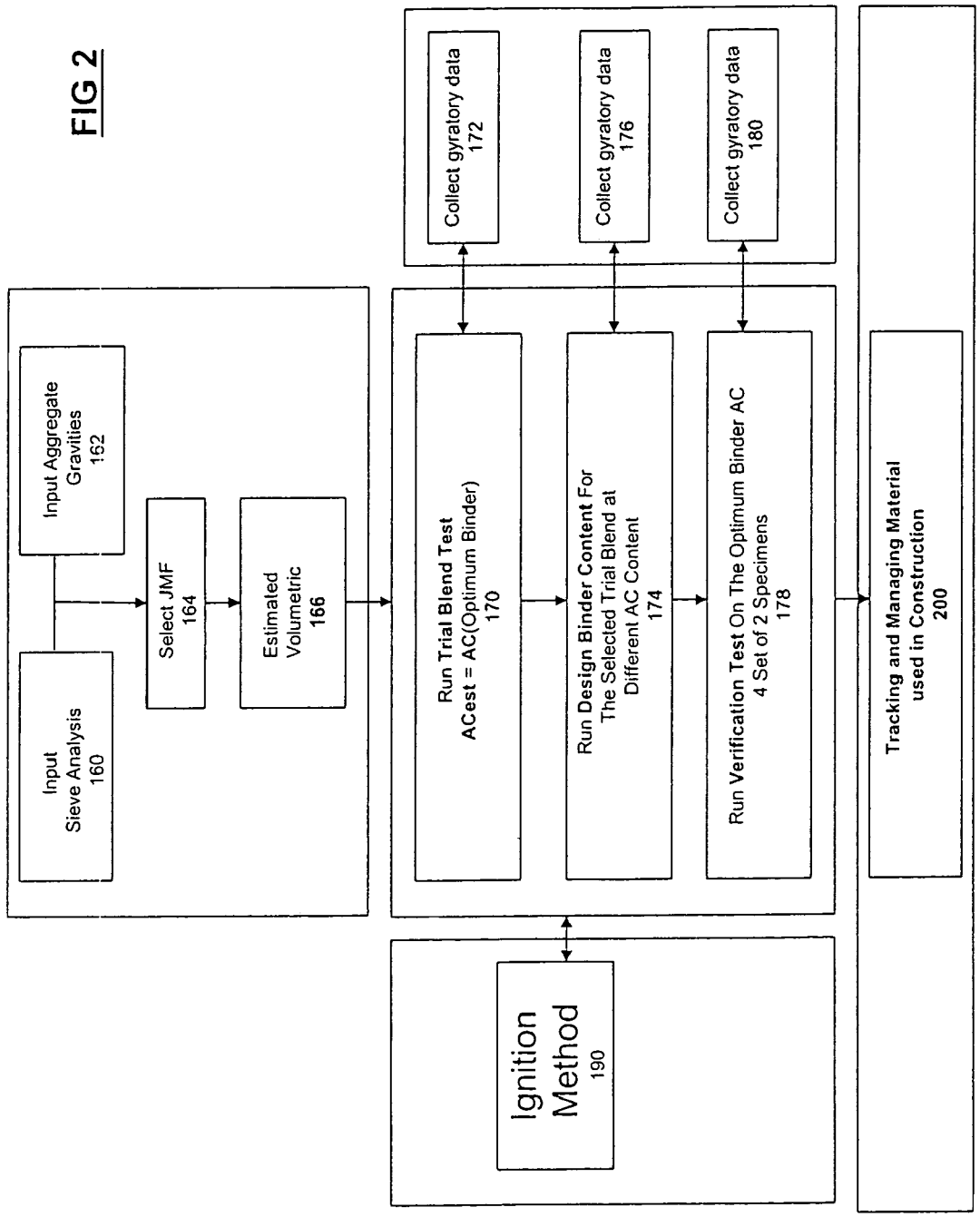

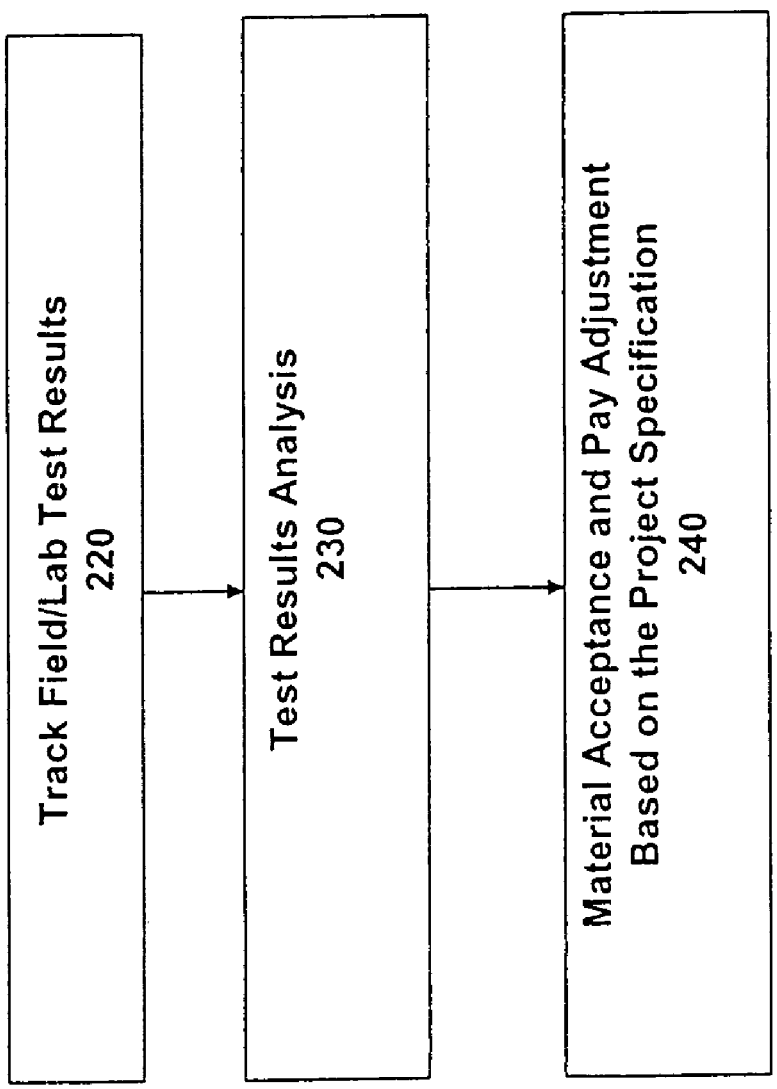

PROCESS CONTROL SYSTEM TO MANAGE MATERIALS USED IN CONSTRUCTION

This application is a continuation of application Ser. No. 10/349,433 filed on Jan. 21, 2003 now U.S. Pat. No. 6,889,148, the content of which is incorporated by reference.

BACKGROUND

The invention relates to a process control system to manage materials used in construction.

In many large-scale construction projects, a developer needs to provide construction bid specification preparation, which is evaluated before the developer is awarded a contract. Once the developer receives the contract, various construction management and contract administration practices need to be implemented. These practices include maintaining an appropriate level of quality assurance. Quality assurance in construction activity relates to proper architectural and structural design, use of good materials and components supplied by various producers, contractors and sub-contractors, proper workmanship in the execution of works by the contractor/sub-contractor, and ultimately proper care during the construction.

The need for quality assurance becomes even more important for governmental projects and is usually mandated by law for an incorporated political unit or municipality or community. For these customers, a construction project must satisfy all states specification. The quality of construction materials should result in satisfactory strength, serviceability and long term durability so as to lower the overall life-cycle cost.

SUMMARY

Systems and methods are disclosed for designing and tracking construction material usage by estimating volumetric properties for one or more mix designs; determining an optimum mix based on laboratory data; and field testing a sample of the optimum mix; and tracking and managing construction material usage based on the optimum mix.

Implementations of the above aspect may include one or more of the following. The system can track laboratory and field test results. For example, it can track Aggregate Properties and Asphalt Properties, and Hot mix Asphalt Properties. The system can analyze the test result. The analysis includes generating a Control Chart as well as calculating statistical measures including Average, Standard deviation, and Range. The system can perform Material Acceptance and Pay Adjustment based on a project specification. Exception reports can be generated.

In another aspect, a system includes a gyratory compactor; a computer coupled to the gyratory compactor, the computer having computer readable code to estimate volumetric properties for one or more mix designs; run one or more tests on the mix design using the gyratory compactor; digitally collect data for each gyration from the gyratory compactor; and select an optimum mix based on the gyration data; an asphalt content tester coupled to the computer to provide ignition data to test the mix; and computer code to track and manage construction material usage based on the optimum mix.

Implementations of the system can include code to: track laboratory and field test results; to analyze the test results; and to perform Material Acceptance and Pay Adjustment based on a project specification.

Advantages of the system may include one or more of the following. The system improves the efficiency of the user by minimizing the use of laboratory trial and error procedures. The system manages, controls and analyzes material test results. It also supports plotting of control charts, arid computing price reduction factors for construction materials projects. The system aids users in construction to have high production level, and reduce cost.

BRIEF DESCRIPTION OF THE FIGURES

FIG. 1 s,hows a process for designing and tracking/managing construction material usage.

FIG. 2 shows one embodiment of the process of FIG. 1.

FIG. 3 shows a process for tracking and managing construction material usage in the process of FIG. 2.

DESCRIPTION

FIG. 1 shows a process for designing and tracking construction material (such as asphalt mixture) usage. First, volumetric properties are estimated (10). Next, a mix is designed (12). The mix can be the Superpave mix. During this process, gyratory data is automatically collected (20). The final mix is optimized by determining an optimum mix based on laboratory data (30). The process then field tests a sample of the optimum mix (40); and tracks/manages construction material usage based on the optimum mix (50).

Referring now to FIG. 2, one embodiment for a construction project management process is illustrated. The inputs to the process of FIG. 2 include performing sieve analysis (160) and inputting gravities data (162). The inputs received from blocks 160 and 162 are used to select a job mix formulation (JMF) (164). A variety of tools, including a graphical data entry tool, a computer optimized data entry tool, a forced data entry tool, and the manual data entry tool, are provided to select the JMF in block 164. Promising JMFs could be quickly evaluated using the estimation process provided by the present invention. JMFs which do not promote compliance of desired specifications can be quickly eliminated from expensive laboratory testing, saving the user time, labor and money. Thus, the present invention uses basic engineering properties to evaluate the proposed JMF and to test the proposed JMF for verification of the desired volumetric properties and to optimize the binder content. The present invention thereby allows the user to rapidly determine whether the proposed JMF, including the combination of aggregates and asphalts that defines the actual gradation and asphalt content to be obtained in the finished construction, satisfies the mixture design. The output of the JMF selection block 164 is provided to estimate volumetric properties with estimated AC Content @4% Air Void (166).

Next, the process of FIG. 1 performs laboratory verification of various proposed JMF solutions that may satisfy the requirements. First, a trial blend test is run based on estimated AC Content @4% Air Void (170). The test uses data collected by a compactor control process of FIG. 1 (172). Based on the trial blend test, a trial blend is selected.

A design binder content test is run for the selected trial blend (174). The content test requests the process of FIG. 1 to generate gyratory data for the selected trial blend (176). Based on the design Binder Content test, an optimum binder is selected. From this selection, a verification test is run on the optimum binder (178). The verification test uses new gyratory data for the optimum binder. An asphalt content tester coupled to the computer to provide ignition data to test the mix (190).

Next, am illustrative Superpave Level I Mix Design procedure is discussed. By, asphalt and aggregate materials that meet their respective criteria are selected. The asphalt binders performance specification is based on the climate and attendant pavement temperatures in which the binder is expected to serve. Physical property requirements remain the same, but the temperature at which the binder must attain the physical properties change. The aggregate physical properties may be specified as coarse aggregate angularity, fine aggregate angularity, flat elongated particles, or by clay content, for example. Several trial blends are generated to meet Superpave gradation requirements (Coarse,Intermediate, Fine). Superpave uses the 0.45 power gradation chart with control limits and a restricted zone to develop a design aggregate structure. The aggregate Blend gradation may pass between the control points while avoiding the restricted zone. The maximum density gradation is drawn from 100% passing the maximum aggregate size through the origin.

Asphalt is blended with trial blends aggregate and run gyratory trial blend. Based on the volumetric test results, the best blend meeting the Superpave Level I Specification is selected. Gyratory compaction test for the selected trial aggregate blend is performed with various design binder contents, and calculate the optimum binder at, for example, a 4% Air void from volumetric test results.

From the Run Verification Test On The Optimum Binder AC operation 178, a quality assurance process 200 is performed. In one embodiment, the process 200 performs Tracking and Managing Material used in Construction.

FIG. 3 shows in more detail the exemplary construction project quality assurance process 200. The process 200 first receives test results from one or more sources, for example laboratory tests and field tests (220). The test results track laboratory and field test results for Aggregate Properties.

Asphalt Properties.

Hot mix Asphalt Properties.

In one embodiment, a user, such as an engineer, verifies conformance to contract specifications by independent sampling and testing during the construction and the production. In this example, the system assists a user to perform the following:

1. Stratified random samples are used to make sure all samples are not concentrated in one section of the area to be sampled. This method ensures random-sampling for each sublots which make up the lot. A lot can be 5000 linear feet of pavement, and that the sample consists of 5 cores per lot, sublot size 1000 linear feet.
2. Data Analysis per lot. The system provides a number of statistical determinations for the user, including:

Average Value of Sublots $$\mu = \frac{\sum x_i}{n}$$

Standard Deviation $$\sigma = \sqrt{\frac{\sum (x_i - \mu)^2}{n-1}}$$

Coefficient of Variation $$cv = 100 \times \frac{\sigma}{\mu}$$

Range of Sublots $R = \text{Max} - \text{Min}$

Next, the process performs a Test Result Analysis (230). In one embodiment, the analysis can perform the following.

Control Chart.

Calculation Average, Standard deviation, Range, among others.

Quality Control charts are plotted to increase efficiency in production. Benefits of Control Charts are: Early detection of trouble; Decrease variability; and Save a permanent record of quality.

Next, the process generates Material Acceptance and Pay Adjustment based on the project specification (240). To illustrate, in one embodiment, the Material Acceptance and Pay Adjustment is determined based on the project specification as follows.

Acceptance plan including the following factors: Method of tests, Lot Size, number of sublots per lot, Acceptance limits.

(PWL) percent with in limits is calculated to check compliance.

Quality Index (Q) is used to estimate the PWL.

a) $Q_L$, $Q_U$ Lower and upper Quality Index are calculated $$QL = \frac{\mu - LL}{\sigma}$$

$$QU = \frac{\mu - UL}{\sigma}$$

b) PL, PU percent out of limit is calculated based on $Q_L$, $Q_U$.

c) PD Total percent out of limit or percent defective $PD = PL + PU$ d) PWL.

$PWL = 100 - PD$ e) Pay factor or Pay Adjustment based on the project specification.

Based on the (PWL) project specification pay factor of each lot is calculated. Payment to the contractor for the lot will be subject to compensation adjustment $CAF = PFc - 1$ CAF: Compensation Adjustment Factor.

PFc: Pay Factor based on (PWL) Project Specification.

The amount of the compensation adjustment will be calculated as the product of:

1) The Compensation Adjustment Factor CAF.
2) The Total tones represented in the lot.
3) Contract unit price per tonne for the contract item involved.

If the compensation adjustment is negative value, the amount of compensation adjustment will be deducted from any money due, the contractor under the contract.

If the compensation adjustment is positive value, the amount of compensation adjustment will be added from any money due, the contractor under the contract.

As shown above, the process of FIG. 3 manages, controls and analyzes material test results. It also supports plotting of control charts, and computing price reduction factors for construction materials projects.

The above processes can be implemented as software running on a computer. The preferred software embodiment worlds with Microsoft's Windows operating system, including Windows-98, Windows-NT and Windows-XP, although any other suitable graphical operating system such as MacOS and Solaris can be used. Windows is a graphical-based operating environment, also known as a graphical user interface, or (GUI) that allows multitasking of programs. In Windows, the computer screen operates like a desktop, allowing instantaneous access to clocks, spreadsheets, word processing, communication software, graphics packages and, of course, this mix design program. The user is able to select rapidly among those applications, as well as any others developed for the environment. The ability to work simultaneously on several different projects more closely approximates the manner in which most people work. However, the user can work in one program at a time if desired. Preferably, the software of the invention is an object-oriented software constructed from Visual Basic, although it can be written in a number of other languages.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for designing and tracking construction material usage, comprising:
   estimating volumetric properties for one or more mix designs;
   determining an optimum mix of raw materials based on laboratory data; and
   field testing a sample of the optimum mix of raw materials based on one or more of: aggregate property, asphalt property, hot mix asphalt property;
   tracking and managing construction material usage based on the optimum mix; and
   adjusting compensation based on a compensation adjustment factor (CAF)

$$CAF = PFc - 1$$

where a Pay Factor (PFc) is based on a Project Specification.

2. The method of claim 1, further comprising tracking laboratory and field test results.

3. The method of claim 2, further comprising tracking Aggregate Properties.

4. The method of claim 2, further comprising tracking Asphalt Properties.

5. The method of claim 2, further comprising tracking Hot mix Asphalt Properties.

6. The method of claim 1, further comprising analyzing the test result.

7. The method of claim 6, further comprising generating a Control Chart.

8. The method of claim 6, further comprising calculating statistical measures including Average, Standard deviation, and Range.

9. The method of claim 1, further comprising performing Material Acceptance and Pay Adjustment based on a project specification.

10. The method of claim 1, further comprising generating exception reports.

11. A system, comprising:
    a gyratory compactor;
    a computer coupled to the gyratory compactor, the computer having computer readable code to estimate volumetric properties for one or more mix designs; run one or more tests on the mix design using the gyratory compactor; digitally collect data for each gyration from the gyratory compactor; and select an optimum mix based on the gyration data; and
    an asphalt content tester coupled to the computer to provide ignition data to test the mix; and
    computer code to track raw materials based on one or more of: aggregate property, asphalt property, hot mix asphalt property and manage construction material usage based on the optimum mix and adjust compensation based on a compensation adjustment factor (CAF)

$$CAF = PFc - 1$$

where a Pay Factor (PFc) is based on a Project Specification.

12. The system of claim 11, wherein the code to track and manage construction material usage further comprises code to: track laboratory and field test results; to analyze the test results; and to perform Material Acceptance and Pay Adjustment based on a project specification.

13. The system of claim 12, further comprising code to track Aggregate Properties.

14. The system of claim 12, further comprising code to track Asphalt Properties.

15. The system of claim 12, further comprising code to track Hot mix Asphalt Properties.

16. The system of claim 15, further comprising code to generate a Control Chart.

17. The system of claim 11, further comprising code to track laboratory and field test results.

18. The system of claim 11, further comprising code to analyze test result.

19. The system of claim 18, further comprising code to calculate statistical measures including Average, Standard deviation, and Range.

20. The system of claim 11, further comprising code to perform Material Acceptance and Pay Adjustment based on a project specification.

* * * * *